United States Patent [19]
Aquila et al.

[11] Patent Number: 6,156,926
[45] Date of Patent: Dec. 5, 2000

[54] PREPARATION OF ACETATES OF HYDROXYL GROUP-CONTAINING ORGANICS, IN PARTICULAR LINALYL ACETATE

[75] Inventors: Werner Aquila, Mannheim; Roland Pox, Ludwigshafen; Heinz Etzrodt, Neustadt, all of Germany

[73] Assignee: BASF Aktiengesellschaft, Ludwigshafen, Germany

[21] Appl. No.: 09/281,954

[22] Filed: Mar. 31, 1999

[30] Foreign Application Priority Data

Apr. 9, 1998 [DE] Germany .......................... 198 15 833

[51] Int. Cl.$^7$ ...................................................... C07C 7/30
[52] U.S. Cl. ............................................ 560/211; 560/205
[58] Field of Search ...................................... 560/205, 211

[56] References Cited

U.S. PATENT DOCUMENTS

| | | | |
|---|---|---|---|
| 3,783,136 | 1/1974 | Inukai et al. | 554/162 |
| 3,966,798 | 6/1976 | Intille et al. | 560/205 |
| 4,529,810 | 7/1985 | Stoutamire | 560/105 |
| 4,691,020 | 9/1987 | Ruechardt et al. | 546/341 |
| 4,940,813 | 7/1990 | Corley et al. | 560/103 |

FOREIGN PATENT DOCUMENTS

| | | |
|---|---|---|
| 1 643 714 | 4/1971 | Germany . |
| 1 239 436 | 7/1971 | United Kingdom . |

*Primary Examiner*—Paul J. Killos
*Assistant Examiner*—Taylor V. Oh
*Attorney, Agent, or Firm*—Oblon, Spivak, McClelland, Maier & Neustadt, P.C.

[57] ABSTRACT

A process for the preparation of acetates of alcohols or phenols, in particular linalyl acetate, by causing alcohols or phenols to react with ketene in the presence of a catalyst, wherein the reaction is carried out using approximately equimolar amounts of linalool and ketene in the presence of a zinc salt of a carboxylic acid, or alternatively in the presence of a zinc compound which forms zinc acetate under the conditions of the reaction, and with vigorous mixing of the reaction mixture.

Using this process, linalyl acetate and numerous other acetates interesting as perfumes or active agents can be obtained to a good degree of purity in yields of more than 90% of theory and in very good space-time yields.

13 Claims, No Drawings

PREPARATION OF ACETATES OF HYDROXYL GROUP-CONTAINING ORGANICS, IN PARTICULAR LINALYL ACETATE

The invention relates to an improved process for the manufacture of acetates of alcohols and phenols, in particular linalyl acetate, by reaction with ketene in the presence of catalysts.

The esters of monocarboxylic acids such as acetic acid are generally fragrant compounds which occur, inter alia, in essential oils. Due to the olfactory properties thereof, many esters of higher alcohols have attained significance in the perfume industry. This particularly applies to 3,7-dimethyl-1,6-octadien-3-yl acetate (linalyl acetate) of formula I

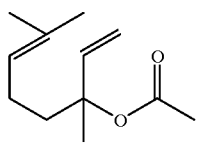

with its fresh-flowery fragrance reminiscent of bergamot oil.

Thus many attempts have been made to find advantageous processes for the preparation of linalyl acetate in the laboratory as well as on an industrial scale. The best known processes for the preparation of esters of higher alcohols comprise the reaction of alcohols with carboxylic halides or carboxylic anhydrides. A drawback occurring in their reaction with carboxylic halides is that during the reaction thereof hydrohalic acids are formed which generally lead to corrosion problems and cause the elimination of water in the case of tertiary alcohols and thus cause polymerizations in many instances.

A drawback occurring in their reaction with carboxylic anhydrides is that in the reaction mixture there are formed equimolar amounts of the corresponding carboxylic acid, which unfavorably influences the equilibrium during esterification and therefore has to be constantly removed from the reaction mixture, which increases costs considerably on an industrial scale.

The preparation of acetates is also known to be possible by the reaction of hydroxyl group-containing compounds with ketene in the presence of catalysts. However, according to Angewandte Chemie Vol. 68, [1956] pp 361 to 363, there occur only non-quantitative acylations with ketene, particularly in the case of higher alcohols, since the resulting acylation product suppresses further reaction. According to said reference the catalysts used are predominantly Lewis acids, such as sulfuric acid, p-toluenesulfonic acid, orthophosphoric acid, boron trifluoride, boron trifluoride etherate or potassium hydrogensulfate. However, since these catalysts are strongly ionized acids or, such as in the case of boron trifluoride, yield strongly acidic secondary products in the presence of traces of water, they can bring about corrosion in metallic apparatus. In addition, the acid catalysts cause the formation of resinous products in some cases (cf The Journal of General Chemistry of the U.S.S.R. Vol. 21, [1951] pp 1147).

Another drawback of these catalysts is the fact that satisfactory separation of the resulting esters from the catalysts can be effected only by distillation. Alkaline catalysts such as urea and certain salts of acetic acid, the use of which as catalysts for acetylation of compounds containing hydroxyl groups with ketene is described in Angewandte Chemie Vol. 68, (1956) pp 363, also suffer from this drawback.

It is also known that it is possible to acetylate alcohols with ketene in the presence of an ion exchanger containing sulfonic acid groups (cf Japanese Patent Application 8334/65). However the ion exchangers also suffer from the drawback that they may be partially dissolved by the starting materials. The yields achieved by this process are, for example, only approximately 83% for the conversion of linalool to linalyl acetate.

To overcome the drawbacks of the above prior art, DE-OS 1,643,712 recommends the reaction of alcohols with ketene in the presence of aluminum silicates having exchangeable cations. This process, which is advantageous for the preparation of acetates of primary alcohols, suffers from a serious drawback concerning the preparation of acetates of tertiary alcohols such as linalyl acetate in that only unsatisfactory conversions are attained despite the use of very large amounts of a specific highly active catalyst (according to DE-OS 1,643,712, the catalyst is used in amounts of from 3 to 800 wt. %, based on alcohol).

Furthermore, Perfum. Essent. Oil Record 58(12), (1967) pp 872–78 reveals that linalyl acetate can be prepared by introducing ketene into linalool at from 20° to 30° C. if 0.2 wt. % of p-toluenesulfonic acid, 0.3 wt. % of orthophosphoric acid or 5 wt. % of an acidic cation-exchange resin are used as catalyst. A drawback of this otherwise good process is that the yields of pure linalyl acetate suitable for olfactory purposes are only from approximately 80 to 85% and that only very low space-time yields are attained. Thus reaction times of from 4 to 5 hours are required, for example, for the reaction of 55 g of linalool.

It is thus an object of the present invention to provide a process for the preparation of linalyl acetate by causing the reaction of linalool with ketene in the presence of catalysts, which makes it possible to prepare linalyl acetate in the laboratory as well as on an industrial scale in an advantageous manner in very good yields, space-time yields and degrees of purity, whilst avoiding the drawbacks of the known processes. This novel process should also be universally applicable to other hydroxyl group-containing organics.

Accordingly, the invention relates to a process for the preparation of acetates by the reaction of organic compounds containing one or more hydroxyl groups with ketene in the presence of catalysts, which is characterized in that the reaction is carried out using a molar amount of ketene approximately corresponding to the number of hydroxyl groups present in the organic compound in the presence of zinc salts of carboxylic acids or alternatively in the presence of zinc compounds which form zinc acetate under the conditions of the reaction, with vigorous mixing of the reaction mixture, in particular to a process for the preparation of linyl acetate by the reaction of linalool with ketene in the presence of catalysts, which is characterized in that the reaction is carried out using approximately equimolar amounts of linalool and ketene in the presence of zinc salts of carboxylic acids or alternatively in the presence of zinc compounds which form zinc acetate under the conditions of the reaction, with vigorous mixing of the reaction mixture.

Particularly good yields are obtained when the reaction is carried out in the presence of zinc salts of carboxylic acids having from 2 to 18 carbon atoms. Specific examples thereof are zinc acetate and zink stearate, particularly zinc acetate, which is relatively readily available. Theoretically, zinc salts of dicarboxylic acids such as succinic acid and oxalic acid or of amino acids such as alanine or leucine may be used, if desired, but no further advantage is gained thereby.

In addition, good yields are attained when the reaction is carried out in the presence of compounds which form zinc acetate under the conditions of the reaction. Of these compounds, zinc oxide is a particularly noteworthy example.

Another very advantageous feature of the process of the invention is that the catalysts need only be used in very small amounts, which makes the process cheaper and facilitates purification of the reaction mixture. The zinc salts are generally used in amounts of from 0.1 to 1.0 wt. % and preferably from 0.2 to 0.5 wt. %, based on alcohol used.

It is very surprising to find that the zinc compounds claimed can be used to such advantage as catalysts, since only extremely unsatisfactory yields are attained with, say, sodium acetate, which is known to be effective as a catalyst for reactions with ketene (cf Comparative Example 1), and the acetates of metals such as silver, aluminum, magnesium, calcium, manganese(II), cobalt, nickel or iron(II) are virtually incapable of catalyzing the reaction (cf Comparative Examples 2 to 9).

Since excess ketene can lead to innumerable side reactions, the process of the invention only provides good yields when the reaction is carried out using approximately equimolar amounts of ketene since linalool tends to take part in side reactions during said conversion.

Since ketene is an extremely reactive compound which strongly tends toward dimerization with the formation of diketene, freshly synthesized ketene is generally used. For the industrial manufacture of ketene there are substantially two routes available: the thermal decomposition of acetone and the thermal decomposition of acetic acid.

The process of the invention gives particularly advantageous results when ketene is used which has been synthesized, just prior to the reaction defined in the present invention, by thermal decomposition of acetic acid at temperatures ranging from 800° to 900° C. and preferably from approximately 850° to 870° C. under a reduced pressure ranging from approximately 700 to 900 mbar and preferably from 750 to 850 mbar.

In order to introduce the resulting ketene into the reaction vessel used for the reaction of the invention in a simple manner, it is of advantage to carry out the reaction under reduced pressure, which is also advantageous for the reaction itself.

The reaction of the invention is generally carried out at temperatures of from approximately 35° to 110° C., preferably from 70° to 100° C., and more preferably from 85° to 95° C., under reduced pressures of from approximately 400 to 900 mbar and more preferably from 500 bis 600 mbar.

It is surprising to find that the reaction is successful at such high temperatures with yields exceeding 90% of pure linalyl acetate, since it is stated in the aforementioned reference Perfumery and Essential Oil Record (London) 58, (12), (1967) page 875 left column, line 22 to right column, line 5, that the formation of by-products rises steeply when the temperature is allowed to rise to 50° C. and that at temperatures of 50° C. the yields of linalyl acetate drop to approximately 27% of theory.

The reaction times in the process of the invention are substantially lower than in the last-named process of the prior art. Whilst reaction times of from 4.5 to 5 hours are necessary when using the process that is described in Perfumery and Essential Oil Record 58, (12) for the conversion of 55 g of linalool, the process of the invention makes it possible to convert approximately 1300 kg of linalool to linalyl acetate over a period of only about 3 hours (cf Example 4).

The acetylation process of the invention is universally applicable to organics containing one or more hydroxyl groups. As examples of suitable hydroxyl group-containing organic compounds there may be mentioned primarily monohydric satutated and unsaturated aliphatic, aromatic/aliphatic or cycloaliphatic/aliphatic alcohols containing from 5 to 20 carbons. The process is particularly significant with respect to tertiary saturated or unsaturated aliphatic, aromatic/aliphatic or cycloaliphatic/aliphatic alcohols containing from 5 to 20 carbons, which are generally relatively difficult to esterify.

However organic compounds containing phenolic hydroxyl groups, such as α-tocopherol, can also be acetylated to advantage by the process of the invention.

As examples of particularly suitable primary alcohols there may be mentioned 2-methyl-2buten-1-ol (prenol), 4-tert-butylcyclohexyl-2-ethanol, 3-tert-butyl-4-methoxycyclohexylmethanol, 2-cyclododecylpropanol (hydroxyambran), phenylethyl alcohol and cyclohexyl-2-ethanol.

As examples of particularly suitable tertiary alcohols there may be mentioned 3-hydroxy-3,7-dimethyloctane (tetrahydrolinalool), 7-hydroxy-3,7-dimethyloctanol (hydroxycitronellal), phenyidimethylcarbonol and 3-hydroxy-3,7-dimethyl-1,6-octadiene (linalool).

The reaction of the invention is advantageously carried out in a suitable reaction vessel comprising, as essential parts, a good stirring and/or mixing unit, a dosing mechanism for ketene, a heating device for initiating the reaction and maintaining the reaction temperature during the subsequent reaction, cooling means for dissipating the heat of reaction occurring in the exothermic conversion, and a vacuum pump. However if the ketene is injected into the reaction vessel, mechanical mixing of the reaction mixture is no longer necessary.

To achieve optimal control of the reaction, it is essential that the ketene be metered in at such a rate that it is never present in excess in the reaction mixture and that the reaction mixture is well agitated at all times.

Hitherto, acetylations with ketene have not achieved any great significance in the perfume industry. Presumably, negative experience with ketene has been a contributary factor here, since overdoses of ketene cause marked discoloration and resinification of the reaction mixture.

To achieve advantageous execution of the process of the invention it is therefore important not to feed in the ketene at an excessively high rate and to stop the reaction at a clearly defined end point.

Using the process of the invention, it is possible to prepare linalyl acetate, which is a desirable product for the perfume industry, and numerous other acetates of alcohols or phenols, such as α-tocopherol, interesting as perfumes or active agents, in an industrially relatively simple manner and in high purities and nevertheless in excellent yields and space-time yields.

EXAMPLE 1 AND COMPARATIVE EXAMPLES 1 TO 11

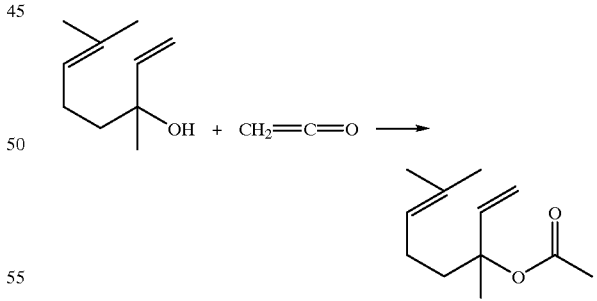

To 616 g (4.0 mol) of linalool there were added, in each case, approximately 1.23 g of zinc acetate or 0.2 wt. %, based on linalool, of the catalyst listed in Table 1 in a stirred vessel under a blanket of nitrogen and with vigorous stirring (disc stirrer: 500 rpm) and from approximately 80 to 100 g/h of freshly prepared ketene were metered in at a temperature between 80° and 95° C. under a pressure of ca 500 mbar with vigorous stirring and brine cooling. In each case, the reaction was stopped when no more ketene was absorbed by the reaction mixture.

The reaction mixture obtained was examined gas-chromatographically.

Table 1 below indicates the catalysts used, the reaction times and the composition of the reaction mixture, as determined by gas chromatography.

TABLE 1

| Ex./Comp. Ex. | Catalyst | Reaction time [min] | Absorbed ketene [mol] | Linalool [%] | Dihydro linalool [%] | Linalyl acetate [%] | Dihydro-linalyl acetate [%] | Unknown by-products [%] | Yield of linalyl acetate [%] |
|---|---|---|---|---|---|---|---|---|---|
| 1 | zinc acetate* | 143 | 6.02 | 0.56 | — | 97.0 | 1.49 | 0.95 | 98.45 |
| Comp. 1 | copper acetate | 142 | 4.12 | 8.24 | — | 84.97 | 1.25 | 5.54 | 85.51 |
| Comp. 2 | cadmium acetate | 105 | 3.43 | 14.78 | — | 82.9 | 1.21 | 1.11 | 80.36 |
| Comp. 3 | sodium acetate | 140 | 2.69 | 70.34 | — | 22.38 | — | 6.95 | 21.85 |
| Comp. 4 | silver acetate | 30 | 0.52 | 92.43 | 0.97 | 5.49 | 0.06 | 1.05 | 4.47 |
| Comp. 5 | aluminum acetate | 20 | 0.14 | 96.32 | 1.07 | 1.85 | — | 0.76 | 1.46 |
| Comp. 6 | magnesium acetate | 30 | 0.33 | 94.79 | 1.01 | 3.0 | 0.06 | 1.14 | 2.42 |
| Comp. 7 | calcium acetate | 30 | 0.21 | 96.63 | 0.88 | 1.66 | 0.03 | 0.80 | 1.32 |
| Comp. 8 | manganese (II) acetate | 30 | 0.33 | 95.31 | 0.63 | 3.59 | — | 0.47 | 2.88 |
| Comp. 9 | cobalt acetate | 30 | 0.28 | 93.71 | 0.69 | 5.24 | — | 0.36 | 4.19 |
| Comp. 10 | nickel acetate | 70 | 0.79 | 92.56 | 0.49 | 5.46 | — | 1.49 | 4.51 |
| Comp. 11 | iron acetate | 30 | 0.24 | 97.37 | 0.20 | 1.96 | — | 0.47 | 1.56 |

*only 0.05 wt % of catalyst

EXAMPLES 2 AND 3 AND COMPARATIVE EXAMPLES 12 AND 13

To 616 g (4.0 mol) of linalool there were added, in each case, approximately 0.05 wt. %, based on linalool, of the zinc compound listed in Table 2 in a stirred vessel under a blanket of nitrogen and with vigorous stirring (disc stirrer: 500 rpm) and from 80 to 100 g/h of freshly prepared ketene were metered in at a temperature of approximately 90° under a pressure of ca 500 mbar with vigorous stirring and brine cooling.

In each case, the reaction was stopped when no more ketene was absorbed by the reaction mixture.

The reaction mixture obtained was examined gas-chromatographically.

Table 2 below indicates the zinc compounds used, the reaction times and the composition of the reaction mixture, as determined by gas chromatography.

EXAMPLE 4

In a stirred-tank reactor there were placed 1305 kg (8474 mol) of linalool under a blanket of nitrogen, to which 0.6 kg (0.05 wt. %, based on linalool used) of zinc acetate were added, whereafter the pressure in the stirred-tank reactor was reduced to 500 mbar with vigorous stirring and the contents of the reactor were heated to 85° C. 500 kg of ketene were then metered in over a period of 3 hours whilst maintaining a reaction temperature of approximately 90° C. by cooling with brine. The reaction mixture was then let down to atmospheric pressure with nitrogen and the reaction was then allowed to continue at 90° C. for a further 30 minutes, approximately, under a blanket of nitrogen.

The resulting crude linalool was examined gas-chromatographically.

It contained 6.64 wt. % of unconverted linalool 90.49 wt. % of linalyl acetate and 1.24 wt. % of by-products.

The selectivity of the conversion was accordingly 90.26% of theory, based on linalool converted.

| Ex./Comp. Ex. | Zinc compound | Reaction time [min] | Linalool [%] | Linanyl acetate [%] | Dihydrolinanyl acetate [%] | Unknown by-products [%] |
|---|---|---|---|---|---|---|
| 2 | zinc oxide | 130 | 6.64 | 96.49 | 1.63 | 1.24 |
| 3 | zinc stearate | 135 | 0.89 | 96.73 | 1.62 | 0.76 |
| Comp. 12 | zinc chloride | 160 | 7.63 | 78.15 | 3.3 | 10.92 |
| Comp. 13 | zinc sulfate | 150 | 23.1 | 73.3 | 1.47 | 2.13 |

EXAMPLES 5 to 10

Reaction with tertiary alcohols and a-4ocopherol

To the quantities of alcohols listed in Table 3 below zinc oxide was added, in the quantities stated in Table 3, in a vessel equipped with a vigorously active disc agitator, under a blanket of nitrogen. At the temperatures and pressures given in Table 3, the quantities of freshly prepared ketene stated in Table 3 were metered in at a rate of from approximately 80 to 100 g/h while the mixture was vigorously stirred and cooled with brine. In each case, the reaction was stopped when the absorption of ketene ceased.

The amounts of acetate obtained and yield data are also listed in Table 3.

TABLE 3

| Example | Alcohol or α-Tocopherol | Amount [g (mol)] | Ketene Amount [g (mol)] | Zinc acetate [wt %, based on the alcohol] | Reaction temperature [° C.] | Pressure in the reactor [mbar] | Effluent [g] | Yield [% of theory] |
|---|---|---|---|---|---|---|---|---|
| 5 | Tetrahydrolinalool | 474 (3.0) | 130 (3.09) | 0.100 | 105–110 | 545–559 | 604 | 99.6 |
| 6 | Hydroxycitronellal | 602 (3.5) | 151 (3.6) | 0.200 | 98–103 | 456–542 | 753 | 87.9 |
| 7 | a-Tocopherol | 605 (1.41) | 61 (1.45) | 0.050 | 118–127 | 474–545 | 666 | not determined* |
| 8 | Phenyldimethyl-carbinol | 680 (5.0) | 207 (4.93) | 0.050 | 83–116 | 463–556 | 887 | 89.6 |
| 9 | Linalool | 770 (5.0) | 211 (5.02) | 0.050 | 80–91 | 502–552 | 991 | 98.2 |
| 10 | Cyclohexylethyl-alcohol | 640 (5.0) | 212 (5.05) | 0.025 | 84–102 | 498–549 | 850 | 94.4 |

*α-Tocopherol distilled in the laboratory. GC analysis of the pure substance revealed a purity of 95.9%

EXAMPLES 11 to 15

Reaction with primary alcohols

To the quantities of alcohols listed in Table 4 below zinc oxide was added, in the quantities stated in Table 4, in a vessel equipped with a vigorously active disc agitator, under a blanket of nitrogen. At the temperatures and pressures given in Table 4, the quantities of freshly prepared ketene stated in Table 4 were metered in at a rate of from approximately 80 to 100 g/h while the mixture was vigorously stirred and cooled with brine. In each case, the reaction was stopped when the absorption of ketene ceased. The amounts of acetate obtained and yield data are also listed in Table 4.

TABLE 4

| Example | Alcohol | Amount [g (mol)] | Ketene Amount [g (mol)] | Zinc acetate [wt %, based on the alcohol] | Reaction temperature [° C.] | Pressure in the reactor [mbar] | Effluent [g] | Yield [% of theory] |
|---|---|---|---|---|---|---|---|---|
| 11 | Prenol | 688 (8.0) | 338 (8.05) | 0.05 | 80–103 | 515 | 1026 | 98.7 |
| 12 | 4-t-Butyl-cyclohexyl alcohol 70/30 | 487 (3.12) | 127 (3.02) | 0.05 | 110–124 | 510 | 614 | 97.8 |
| 13 | 3-t-Butyl-4-methoxy cyclohexyl methanol | 402 (2.01) | 85 (2.02) | 0.05 | 86–105 | 513 | 488 | 99.6 |
| 14 | Hydroxyambran | 752 (3.33) | 139 (3.3) | 0.10 | 92–135 | 500 | 891 | 98.2 |
| 15 | Phenylethyl alcohol | 610 (5.0) | 220 (5.24) | 0.05 | 96–102 | 512–586 | 981 | 99.1 |

We claim:

1. A process for the preparation of an acetate by the reaction of an organic compound containing one or more hydroxyl groups with ketene in the presence of a catalyst, wherein the reaction is carried out using a molar amount of ketene which approximately corresponds to the number of hydroxyl groups in the hydroxy group-containing compound in the presence of a zinc salt of a carboxylic acid, or alternatively in the presence of a zinc compound which forms zinc acetate under the conditions of the reaction, and with vigorous mixing of the reaction mixture.

2. A process as defined in claim 1, wherein the reaction is effected in the presence of zinc acetate or a zinc compound which forms zinc acetate under the conditions of the reaction.

3. A process as defined in claim 1, wherein the organic compound containing one or more hydroxyl groups used is a monohydric satutated or unsaturated aliphatic, aromatic/aliphatic or cycloaliphatic/aliphatic alcohol containing from 5 to 20 carbons, which is caused to react with ketene to form the corresponding acetate.

4. A process as defined in claim 1, wherein the organic compound containing one or more hydroxyl groups used is a tertiary satutated or unsaturated aliphatic, aromatic/aliphatic or cycloaliphatic/aliphatic alcohol containing from 5 to 20 carbons, which is caused to react with ketene to form the corresponding acetate.

5. A process as defined in claim 1, wherein the reaction is caried out using approximately equimolar amounts of linalool and ketene for the production of linalyl acetate.

6. A process as defined in claim 1, wherein the reaction is effected in a reaction vessel comprising a good stirring or mixing unit, a dosing mechanism for ketene, a source of heat for initiating the reaction and for the subsequent reaction, cooling means for the removal of the heat of reaction and a vacuum pump.

7. A process as defined in claim 1, wherein the reaction is effected at temperatures ranging from 35° to 110° C. and pressures ranging from approximately 400 to 900 mbar.

8. A process as defined in claim 1, wherein the reaction is effected at temperatures ranging from 70° to 100° C.

9. A process as defined in claim 1, wherein the reaction is effected under pressures ranging from approximately 500 to 600 mbar.

10. A process as defined in claim 1, wherein ketene is used which has been obtained by thermal decomposition of acetic acid at temperatures ranging fom 800° to 900° C. and pressures ranging from 700 to 900 mbar, just prior to the reaction of said organic compound with said ketene.

11. The process of claim 10, wherein said temperature is approximately 850° C.

12. The process of claim 10, wherein said pressure ranges from 750 to 850 mbar.

13. The process of claim 10, wherein said temperature is approximately 850° C. and said pressure ranges from 750 to 850 mbar.

* * * * *